United States Patent [19]
Huc et al.

[11] Patent Number: 5,422,111
[45] Date of Patent: Jun. 6, 1995

[54] POLYOSE/FATTY ACID COMPLEX PRODUCT WITH A HIGH FATTY ACID CONTENT, USE AS AN EMULSIFIER OR MOISTURIZER AND EMULSIFYING OR MOISTURIZING COMPOSITION IN WHICH IT IS PRESENT

[75] Inventors: Alain Huc, Ste Foy les Lyon; Danièle Antoni, Vernaison; Eric Perrier, Vienne, all of France

[73] Assignee: Coletica, Lyons, France

[21] Appl. No.: 113,047

[22] Filed: Jul. 22, 1993

[30] Foreign Application Priority Data

Jan. 23, 1991 [FR] France ................................. 91 00758

[51] Int. Cl.$^6$ ................................................ A61K 7/00
[52] U.S. Cl. ..................................... 424/401; 514/844; 514/847; 514/937
[58] Field of Search ................. 424/401; 514/844, 847, 514/937

[56] References Cited

U.S. PATENT DOCUMENTS 2,749,276 6/1956 Novak et al. ........................ 167/85
4,223,023 9/1980 Furda .................................... 424/80

FOREIGN PATENT DOCUMENTS 2009161 1/1970 France .
0227810 10/1984 Japan .

*Primary Examiner*—Gollamudi S. Kishore
*Attorney, Agent, or Firm*—Millen, White, Zelano, & Branigan

[57] ABSTRACT

The invention relates to a polyose/fatty acid complex product. This complex product is the reaction product of at least one polyose with at least one fatty acid, in particular in the form of a halide or the anhydride. The fatty acid can be saturated or unsaturated and can comprise from 8 to 28 carbon atoms. This complex product has a high moisturizing capacity and, surprisingly, an emulsifying capacity and can be used to prepare valuable cosmetic or pharmaceutical compositions.

26 Claims, No Drawings

POLYOSE/FATTY ACID COMPLEX PRODUCT WITH A HIGH FATTY ACID CONTENT, USE AS AN EMULSIFIER OR MOISTURIZER AND EMULSIFYING OR MOISTURIZING COMPOSITION IN WHICH IT IS PRESENT

This is a continuation-in-part application of PCT/FR92/00054 filed on Jan. 22, 1992, designating US The present invention relates essentially to a polyose/fatty acid complex product with a high fatty acid content, to its use as an emulsifier or moisturizer and to an emulsifying or moisturizing composition in which it is present, especially a cosmetic and/or pharmaceutical composition.

BACKGROUND OF THE INVENTION

It is known that moisturization of the skin remains one of the major objectives of cosmetics. A variety of active ingredients are used for this purpose. They belong to two major categories: the first category comprises low-molecular compounds and the second category comprises high-molecular substances. The first family can have a high moisturizing capacity over a relatively short time, whereas the effect in the case of the second family is less substantial although longer-lasting. Examples of the low-molecular moisturizing substances which may be mentioned are glycerol, urea and the constituents of the natural moisturizing factor (or NMF). The high-molecular moisturizing substances, which are generally of the polymeric type, comprise in particular certain proteins such as collagen.

It is further known that the intercellular cement of the stratum corneum consists of a hydrophobic complex group of lipids made up essentially of free sterols, free fatty acids, triglycerides, glycosphingolipids and ceramides. The hydrophilic molecules used as moisturizers will be repelled by this hydrophobic medium and will have to find their way to the lower layers of the epidermis and especially to the dermis, which contains a large amount of water. Thus the stratum corneum and the upper layers of the epidermis will be influenced very little by moisturizing substances. Now, the impression of dryness of the skin comes from the stratum corneum and the upper layers of the epidermis. It therefore proves important to be able to keep the moisturizing molecules used for as long as possible in these layers.

Document JP-B-46-9327 has described a process for the manufacture of a fatty acid ester of chondroitin sulfate by reacting a fatty acid halide with the free hydroxyl groups in the saccharide part of the chondroitin sulfate. However, the proportion of fatty acid in the reaction product obtained is low. This reaction product does not possess significant moisturizing properties and even less an emulsifying activity. Other similar documents are JP-A-17 566/68, JP-A-02/169684, JP-A-62/238209 and JP-A-02/243611. Document US-A-4 223 023 describes a binder for non-absorbable lipids which is based on chitosan, in particular in the form of fatty acid/chitosan complexes by neutralizing chitosan with fatty acids (column 1, lines 42 to 48). This product is applied as a lipid binder and in particular as a fat extender in margarines and sauces, especially salad dressings (page 2, lines 37 to 41). This product also reduces the calorie contents of the foodstuff (page 2, lines 33 to 36).

NOVAK U.S. Pat. No. 2,749,276 and GILLETTE French Patent FR-A-2,009,161 disclose covalent esters of fatty acid and polyose prepared in an organic medium at a high temperature which are soluble in organic solvents due to a very high content in covalently bond fatty acid groups. This reaction products with a high covalent content in fatty acid groups do not have emulsifying or moisturizing properties.

In the prior art U.S. Pat. No. 2,749,276 and French patent 2,009,161, the proportion of the fatty acid groups linked through covalent bonds with the polyose is ranging between 40 and 80% which impedes that such a product has an emulsifying power, said reaction product having lost the hydrophylic character of the polyose.

SUMMARY OF THE INVENTION

One main object of the present invention is to solve the novel technical problem consisting in the provision of a solution which makes it possible to find novel polyose-based complex products having a high relative proportion of fatty acid, this proportion preferably being equal to at least 10% by weight and particularly preferably equal to at least 15% by weight of fatty acid, based on the polyose.

A further main object of the present invention is to solve the novel technical problem consisting in the provision of a solution which makes it possible to find novel substances which have a high moisturizing capacity and are capable, when applied to the epidermis, of remaining in the stratum corneum and in the upper layers of the epidermis so as to improve the moisturizing effect.

To achieve this object, the inventors came to the idea of creating hydrolipidic complexes consisting of polyoses bound to fatty acids, in particular by a chemical process. Polyoses are found to have a powerful moisturizing capacity which has to be maintained even after reacting it with fatty acids, notably by limiting the content in covalently bound fatty acids to not more than about 10 weight per cent of the total amount of the fatty acids.

After obtaining these hydrolipidic polyose/fatty acid complexes under specific reacting conditions, it was discovered that these novel complexes unexpectedly have emulsifying properties and thereby make it possible to produce emulsions without the addition of another emulsifier.

Thus a further object of the present invention is to solve the novel technical problem consisting in the provision of a solution which makes it possible to provide novel biocompatible emulsifiers such that the use of synthetic surfactants, which always exhibit a greater or lesser degree of toxicity, can be avoided.

A further object of the present invention is to provide novel moisturizing or emulsifying compositions which have an excellent moisturizing or emulsifying capacity and a lower toxicity, allowing frequent use in the area of cosmetics or pharmaceuticals.

Finally, a further object of the present invention is to provide novel cosmetic or pharmaceutical compositions which have a high moisturizing capacity and do not contain synthetic surfactant. Advantageously, these cosmetic or pharmaceutical compositions will take the form of an emulsion without the use of a synthetic surfactant.

All these objects are achieved simultaneously according to the present invention in a manner which is simple and inexpensive and which can therefore be used at the industrial scale.

DETAILED DESCRIPTION OF THE INVENTION

Thus, according to a first feature, the present invention provides a polyose based complex product which is the chemical reaction product of at least one polyose suspended or dissolved in water with at least one fatty acid under a reactive form, said reaction product having subsequently undergone a lyophilization step, said lyophilized reaction product containing less than about 10% by weight of the total amount of fatty acids linked through covalent bonds to said polyose.

According to a particular embodiment the reaction is performed at ambiant or moderate temperature. By moderate temperature, it is meant a temperature relatively close to ambiant temperature, namely below 60° C.

According to an advantageous embodiment, the invention complex product comprises fatty acid groups linked through ionic bonds and also fatty acid groups linked through hydrophobic bonds to said polyose. By hydrophobic bonds, it is meant that the linkage is neither ionic or covalent but is made with an hydrophobic part of the polyose like a Van der Waals linkage. In particular, it is a specific preferred feature of the invention complex product that the fatty acids groups which are linked to the polyose through hydrophobic bonds are under a neutralized form.

Accordingly, it is a preferred embodiment of the invention complex product that the reaction is performed between the fatty acids and the polyose in an aqueous medium which is brought to on initial basic pH, said basic pH being most preferably of a value higher than 7.5 and in particular ranging between 7.5 and 10 and most preferably between 7.5 and 9. After reaction with the fatty acids, the pH which has become acidic in view of the high proportion in fatty acids, is advantageously again brought to a neutral value or a weak basic value not more than about 8.

Due to the presence of several types of bounds between the fatty acid groups and the polyose molecules, namely of the covalent type which is less than about 10%, by weight of the total fatty acids and ionic bonds as well as hydrophobic bonds, the invention complex product maintains the essential hydrophilic character of the polyose.

This provides the positive unexpected technical result that the invention complex product has a strong emulsifying power, notably due to the presence of fatty acid salts resulting from the neutralization of the aqueous reaction medium which is directly used for lyophilization.

In the present invention, the total amount of the fatty acid groups in the complex reaction product is determined by chromotography in vapor phase after methylation with methanol in presence of boron fluoride.

The amount of fatty acid linked through hydrophobic bounds is determined through extraction with ether and the amount of fatty acid groups linked through ionic bounds is determined in the same way as for the hydrophobic bounds, but after a treatment of the complex product within an acid bath at pH 2.

In one particular embodiment, the fatty acid in reactive form is in the form of a fatty acid halide such as the chloride, fluoride or, if need be, iodide, or in the form of the fatty acid anhydride. A fatty acid chloride or the anhydride constitutes the preferred form of the initial fatty acid to be reacted with the polyose.

Advantageously, the above-mentioned polyose is selected from the group consisting of mucopolysaccharides or glycosaminoglycans, particularly structural glycosamines selected from the group consisting of hyaluronic acid, chondroitin 4-sulfate, chondroitin 6-sulfate, dermatan sulfate, heparan sulfate and keratan sulfate, as well as heparin and its derivatives or its fractions of lower molecular weight, which are also called low-molecular heparin, abbreviated to LMH. Heparins of low molecular weight, generally of between 2000 and 10,000, are described for example in patent U.S. Pat. No. 4,486,420 to CHOAY. Other polyoses are dextrane, dextran, amyloses, amylopectins and chitosan.

In one particular variant, the complex product in question is obtained from a crude extract of a terrestrial or aquatic plant, in particular a marine plant, such as an alga, which contains a relatively small proportion of at least one polyose and which is reacted with at least one fatty acid. Such crude extracts are commercially available. It is preferable to use a marine plant extract, in particular a crude extract of ascophyllum algae or laminaria algae.

In another particular variant, the above-mentioned fatty acid consists of any fatty acid which is capable of being bound to a polyose. At the present time, there is no known example of a fatty acid which could not bind to polyoses. This binding can be effected by using the initial fatty acid in the form of a halide or the anhydride. Fatty acids which may be mentioned are all saturated or unsaturated (mono- or poly-unsaturated) fatty acids, in particular those having from 8 to 28 carbon atoms. Particularly advantageous examples of fatty acids are stearic acid, lauric acid, linoleic acid, linolenic acid and undecylenic acid.

In one advantageous variant, the polyose can be used in the form of a polyose/protein mixture. A preferred example of proteins is atelocollagen.

A particularly preferred complex product of the invention is the chondroitin 4-sulfate/stearate complex, as is the chitosan/stearate complex.

The proportions of fatty acid relative to the polyose can vary within wide limits, for example between 0 and 75% by weight. A preferred proportion of fatty acid relative to the polyose is between at least 10 and 75% by weight and preferably between 15 and 75% by weight. Thus the proportion of fatty acid relative to the polyose is very high, it being impossible for this proportion to be obtained simply by a chemical reaction of the polyose with the fatty acid in reactive form. However, all the fatty acid groups are not linked to the polyose through covalent bonds. In fact, not more than about 10% by weight of fatty acid groups are linked to the polyose through covalent boud even after the performing of a lyophilization step. As above said, the non-covalently linked fatty acid groups are linked to the polyose through either ionic bonds or hydrophobic bonds. This is achieved by performing the chemical reaction between the fatty acids and the polyose molecules in an aqueous reacting medium which is preferably brought to an initial basic pH value. Furthermore, before performing the lyophilization step, the reaction medium which has been become acid due to the high amount of fatty acids added, is brought again to a pH substantially neutral or weakly basic namely between about 7 and about 8. In view of the fact that, in the case of the invention, it is preferable to prepare moisturizing or emulsifying products intended for use in the manufacture of cosmetic or pharmaceutical compositions, the pH is preferably brought to neutrality or up to around 8 so as to be at a pH compatible with the physiological pH.

It has been observed that, to obtain a significant moisturizing activity of the polyose/fatty acid reaction product, the relative proportion of fatty acid is advantageously between 10 and 75% by weight and preferably between 15 and 75%. On the other hand, to obtain a significant emulsifying activity of the polyose/fatty acid reaction product, it is preferable to have a fatty acid/polyose ratio of between 50% and 75% by weight.

Furthermore, according to one advantageous characteristic of the invention, the relative proportion of proteins, where present, can vary within wide limits and, for example, can range without limitation from 0 to 75% by weight, based on the weight of the polyose. A particularly valuable source of protein is formed by a conventional, commercially available extract of terrestrial or marine plants such as algae. In fact, in the crude state, such extracts contain essentially a protein/polyose mixture which can be used directly to form the complex product of the invention. These extracts also constitute a practical source of polyoses.

According to a second feature, the present invention relates to the use of the above-mentioned polyose/fatty acid complex product as an emulsifier. In this use, the above-mentioned complex product can be employed in any proportion. Particularly preferred proportions by weight for which an emulsifying effect is obtained vary between 0.1 and 5%. Preferred proportions are of the order of 1 to 3% by weight, based on the total weight of the composition to be emulsified.

According to a third feature, the present invention further relates to the use of the above-mentioned polyose/fatty acid complex product as a moisturizer. This complex product can be used in any proportion which enables this moisturizing effect to be obtained. Particularly preferred proportions again vary between 0.1 and 5% by weight, based on the total weight of the composition to be moisturized.

According to a fourth feature, the present invention further relates to a moisturizing composition which comprises a polyose/fatty acid complex product as defined above.

According to a fifth feature, the present invention further provides an emulsifying composition which contains, as the emulsifier, a polyose/fatty acid complex product as defined above.

According to a sixth feature, the present invention further relates to a cosmetic or pharmaceutical composition, in particular for topical use, which contains a polyose/fatty acid complex product as defined above.

According to yet another feature, the present invention further relates to a method of preparing a polyose based complex product comprising reacting at least one polyose in suspension or dissolved in an aqueous medium such as water with at least one fatty acid under reactive form, in particular in the form of a halide or the anhydride, and then lyophilizing the reaction product to give a polyose/fatty acid reaction product with a high fatty acid content, wherein the proportion by weight of the fatty acid groups linked to the polyose through covalent bonds is less than about 10% by weight with respect to the total amount of said fatty acids.

In one advantageous embodiment, said reaction is performed in an aqueous medium which has been brought to an initial basic value. Due to the high proportion of fatty acids, the adding of fatty acids renders the pH highly acid. It is preferred after the reaction to bring again the pH to a neutral value or a weak basic value, in particular between 7 and about 8 prior to lyophilization. The invention enables to have the presence of fatty acid groups linked through ionic bonds and fatty acid groups linked through hydrophobic bonds. Furthermore, due to the neutral or weakly basic pH after reaction, at least the fatty acid groups which are linked trough hydrophobic bounds to the polyose are under a neutralized form, namely as salts. These salts can be formed from usual cations of basic compounds and notably sodium, potassium without limitation, as it is well known to those skilled in the art. The presence of these salts plays an important role in the emulsifying properties of the invention product.

In the particular case where the polyose/fatty acid complex product is intended for use in the manufacture of cosmetic or pharmaceutical compositions applied to a mammal, in particular a human, the pH of the reaction medium is preferably brought to a substantially neutral value or to a value not more than about 8 so as to be compatible with the physiological pH.

Furthermore, in one particular embodiment of this method, the above-mentioned polyose is suspended or dissolved in water and the fatty acid is added thereto, preferably only when the polyose water medium has been brought to an initial basic pH.

It should be noted that, in one preferred variant, the lyophilization step is only performed when, after reacting the fatty acid with the polyose and the pH is again brought to a substantially neutral value or a weak basic pH value and not more than about 8, the pH has been stabilized at the desired value, which may require a relatively long period of time, possibly of several hours.

The lyophilization step is preferably performed in situ with the reaction medium, namely without any extracting or isolating step. This provides presence of fatty acid groups linked to the polyose through ionic or hydrophobic bonds.

The invention further relates to a method of cosmetic or esthetic treatment of the epidermis, especially an epidermis having a moisture imbalance, which comprises applying a polyose/fatty acid complex product as defined above in an amount which is effective for restoring moisture to the epidermis. The product of the invention improves or restores the plasticity of the epidermis.

As stated above, the polyose/fatty acid complex product according to the present invention has a powerful moisturizing capacity and, unexpectedly, a high emulsifying capacity without the addition of another emulsifier. This complex product thus makes it possible to avoid using a synthetic surfactant, which always exhibits a greater or lesser degree of toxicity. By virtue of the emulsifying capacity, the compositions containing the complex product of the invention are more natural and have an extremely pleasant cosmetic feel. Furthermore, in the case where the polyose used is active on the keratinocyte, it is also observed, unexpectedly, that the complex product according to the invention makes it possible to enhance this property on the epidermis. Also, given that glycosaminoglycans are constituent substances of the connective tissues, the complex product according to the invention is of great value in cosmetology for pharmaceutical applications. In addition to having a powerful moisturizing capacity, this complex product makes it possible to play a part in cell development.

Other objects, characteristics and advantages of the invention will become clearly apparent from the following explanatory description referring to several Examples of the invention, which are given simply by way of illustration and cannot therefore in any way limit the scope of the invention. All the percentages are given by weight, unless indicated otherwise.

EXAMPLE 1

Preparation of the complex product (chondroitin 4-sulfate/stearic acid)

A) - Preparation of chondroitin 4-sulfate

This acid is extracted from the nasal septa of calves. These are first washed carefully in a solution of sodium chloride containing 9 pans per 1000. They are then chopped up and ground. The ground material is then placed in a 0.5N solution of potassium hydroxide at a rate of 1 kg/1. After stirring, the whole is left to stand at room temperature for 24 h. After this period of centrifugation at 30,000 g for 50 min, pure acetic acid is added to the supernatant to neutralize the sodium hydroxide. The solution is then concentrated five-fold by evaporation under vacuum. The concentrate is poured into three times its own volume of ethanol. The precipitate is recovered by decantation and dissolved in softened water. The chondroitin 4- sulfate is obtained by lyophilization of this solution.

B) - Coupling 1 kg of chondroitin 4-sulfate obtained according to A) above is introduced into 10 l of water and dissolved by stirring for 1 h with a centripetal turbine. The pH of the solution is brought to 8.5 with an N solution of sodium hydroxide.

3 kg of stearoyl chloride are then added to the solution of chondroitin 4-sulfate. The whole is stirred with the turbine for 2 h. When the pH is less than or equal to 1, it is brought to 8 using sodium hydroxide, with stirring. The adjustment is effected with an N solution of sodium hydroxide. Several hours are required to stabilize the pH at a value of 8.

When the pH is stable, the mixture is lyophilized under the following conditions:
* Freezing:
  - Temperature: −40° C.,
  - Duration: 3 h.
* Sublimation:
  - Temperature: 25° C.,
  - Pressure: 400 μbar,
  - Duration: 23 h.
* Desiccation to dryness:
  - Temperature: 40° C.,
  - Pressure: 5 μbar,
  - Duration: 3 h.

The lyophilizate obtained can be used to prepare an emulsion.

The composition of the complex product obtained, in lyophilized form, is approximately as follows:
- Chondroitin 4-sulfate: 22%,
- Fatty acid: 65% (as sodium stearate),
- Sodium chloride: 13%.

In this lyophilized invention complex product, the weight proportion of fatty acids linked to the polyose through covalent bonds is of about 7% with regard to the total weight of the fatty acids.

About half of the remaining fatty acid groups was under ionic form. Namely about 46.5 weight % of the total weight of the fatty acids and about the same weight proportion for the fatty acid groups linked through hydrophobic bonds.

EXAMPLE 2

Preparation of a chitosan/stearic acid complex product of the invention

A) - Preparation of chitosan

Chitosan is a commercially available product originating from the deactylation of chitin, a polymer which constitutes the shell of crustaceans.

B) - Coupling 1 kg of chitosan is introduced into 10 l of water, the pH of which is brought to 3 with an N/10 solution of hydrochloric acid. Dissolution is effected by stirring for 1 h with a centripetal turbine. The pH of the solution is then brought to 8.5 with an N solution of sodium hydroxide.

2.3 kg of stearoyl chloride are then added to the solution of chitosan. The whole is stirred with the turbine for 2 h. When the pH is less than or equal to 1, after the reaction time of 2 h, it is brought to 8 using sodium hydroxide, with stirring. The adjustment is effected with an N solution of sodium hydroxide. Several hours are required to stabilize the pH at a value of 8.

When the pH is stable, the mixture is then lyophilized under the lyophilization conditions described in Example 1.

The lyophilizate obtained can be used to prepare emulsions.

The lyophilized complex product has the similar relative proportions in fatty acid covalent bounds, fatty acid ionic bonds and fatty acid hydrophobic bonds as those obtained in example 1.

EXAMPLE 3

Cosmetic or pharmaceutical composition in the form of an emulsion

The formulation of this preparation, obtained from the complex product of Example 1, is given in Table I. The method by which it is obtained is described below:

The aqueous phase A is heated at 80° C., with stirring, until the powdered complex product of the invention, obtained in Example 1, has totally dissolved. This operation takes about ½ h.

At the same time, the fatty phase B is heated at 80° C. for 20 min, with stirring, to obtain complete homogenization.

At 80° C., phase B is added to phase A and the whole is homogenized by ultrasonic agitation for 1 min and then stirred slowly with a centripetal stirrer. Stirring is maintained until the mixture has cooled and become increasingly viscous. When the temperature reaches 30° C., part C is added to the emulsion.

EXAMPLE 4

Cosmetic or pharmaceutical composition in the form of an emulsion

The formulation of this preparation, obtained from the complex product of Example 2, is given in Table II:

It is obtained by the following method:

The aqueous phase A is heated at 80° C., with stirring, until the powdered complex product of the invention, obtained in Example 2, has totally dissolved. This operation takes about 30 min.

At the same time, the fatty phase B is heated at 80° C. for 20 min, with stirring, to obtain complete homogenization.

At 80° C., phase B is added to phase A and the whole is homogenized by ultrasonic agitation for 1 rain and then stirred slowly with a centripetal stirrer. Stirring is maintained until the mixture has cooled and become increasingly viscous. When the temperature reaches 30° C., part C is added to the emulsion.

This technique is of course applicable to all polyoses or polyose/protein mixtures. Complexes using commercially available plant or algae extracts as the source of polyose can thus be prepared.

Finally, it is possible to use a large number of fatty acids, in particular polyunsaturated fatty acids, which can be grafted via:
- either their chloride,
- or their anhydride.

TABLE I

| | Compound | Percentage by weight |
|---|---|---|
| Phase A | Lyophilized complex product of Example 1 | 3 |
| | Carbopol ® | 0 |
| | Water | 77.7 |
| | Propylene glycol | 0 |
| | Glycerol | 5 |
| Phase B | Beeswax | 3 |
| | Lanette 14 ® (1) | 4 |
| | Dragoxat ® (2) | 3 |
| | Solid purcellin ® (2) | 4 |
| Phase C | Silicone | 0.5 |
| | Phenonip ® (3) | 0.5 |
| | Bactericide MB ® (2) | 0.5 |
| | Triethanolamine | 0 |

1 - HENKEL
2 - DRAGOCO
3 - NIPA LABORATORIES

TABLE II

| | Compound | Percentage by weight |
|---|---|---|
| Phase A | Lyophilized complex product of Example 2 | 1 |
| | Carbopol ® | 0.5 |
| | Water | 79.3 |
| | Propylene glycol | 2 |
| | Glycerol | 0 |
| Phase B | Beeswax | 3 |
| | Lanette 14 ® (1) | 3 |
| | Dragoxat ® (2) | 3 |
| | Solid purcellin ® (2) | 3 |
| Phase C | Silicone | 0.5 |
| | Phenonip ® (3) | 0.5 |
| | Bactericide MB ® (2) | 0.5 |
| | Triethanolamine | 1 |

1 - HENKEL
2 - DRAGOCO
3 - NIPA LABORATORIES

What is claimed is:

1. A polyose-complex containing product, said polyose-complex obtained by a process comprising:
   (1) reacting at least one polyose in an aqueous reaction medium, with a sufficient amount of at least one activated fatty acid to obtain a reaction mixture comprising (a) unreacted fatty acid and (b) a reaction product of not more than about 10% by weight of fatty acids linked to the polyose through covalent bonds with regard to the total weight of the fatty acids, and
   (2) subjecting said reaction mixture to lyophilization to obtain said polyose-complex containing product comprising fatty acid linked through covalent bonds to the polyose, and unreacted fatty acid.

2. The product of claim 1, wherein the activated fatty acid is selected from the group consisting of a fatty acid halide and a fatty acid anhydride.

3. The product of claim 1, wherein the polyose is selected from the group consisting of a mucopolysaccharide chitosan, dextran, dextrane, amylose and amylopectin.

4. The product of claim 1, wherein said activated fatty acid has from 8 to 28 carbon atoms.

5. The product of claim 4, wherein said fatty acid which is activated is selected from the group consisting of stearic acid, lauric acid, linoleic acid, linolenic acid and undecylenic acid.

6. The product of claim 1, wherein said polyose is present as a component of a crude extract of an ascophyllum algae or a laminaria algae.

7. The product of claim 1, wherein the polyose-complex containing product further comprises a protein.

8. The product of claim 7, wherein said protein is atelocollagen.

9. The product of claim 1, wherein the proportion of fatty acid is between 10 and 75% by weight of the total of fatty acid and polyose.

10. The product, of claim 1, wherein the proportion of fatty acid is between 15 and 75% by weight of the total of fatty acid and polyose.

11. The product of claim 1, wherein said polyose is present as chondroitin 4-sulfate and said activated fatty acid is stearic acid.

12. The product of claim 1, wherein said polyose is present as chitosan and said activated fatty acid is stearic acid.

13. A moisturizing composition comprising as a moisturizer, a polyose-complex containing product obtained by a process comprising:
   (1) reacting at least one polyose in an aqueous reaction medium, with a sufficient amount of at least one activated fatty acid to obtain a reaction mixture comprising (a) unreacted fatty acid and (b) a reaction product of not more than about 10% by weight of fatty acids linked to the polyose through covalent bonds with regard to the total weight of the fatty acids, and
   (2) subjecting said reaction mixture to lyophilization to obtain said polyose-complex containing product comprising both fatty acids linked through covalent bonds to the polyose and unreacted fatty acid, the proportion of said polyose-complex containing product ranging between 0.1 and 5% by weight with respect to the total weight of said composition.

14. An emulsifying composition comprising as an emulsifier, a polyose-complex containing product obtained by a process comprising:
   (1) reacting at least one polyose in an aqueous reaction medium, with a sufficient amount of at least one activated fatty acid to obtain a reaction mixture comprising (a) unreacted fatty acid and (b) a reaction product of not more than about 10% by weight of fatty acids linked to the polyose through covalent bonds with regard to the total weight of the fatty acids, and
   (2) subjecting said reaction mixture to lyophilization to obtain said polyose-complex containing product comprising both fatty acids linked through covalent bonds to the polyose and unreacted fatty acid, the proportion of said polyose-containing product ranging between 0.1 and 5% by weight with respect to the total weight of said composition.

15. A cosmetic or pharmaceutical composition comprising a polyose-complex containing product obtained by a process comprising:
   (1) reacting at least one polyose in an aqueous reaction medium, with a sufficient amount of at least one activated fatty acid to obtain a reaction mixture comprising (a) unreacted fatty acid and (b) a reaction product of not more than about 10% by weight of fatty acids linked to the polyose through covalent bonds with regard to the total weight of the fatty acids, and
   (2) subjecting said reaction mixture to lyophilization to obtain said polyose-complex containing product comprising both fatty acids linked through covalent bonds to the polyose and unreacted fatty acid.

16. The composition of claim 15 wherein the proportion of the polyose-complex containing product ranges between 0.1 and 5% by weight with respect to the total weight of the composition.

17. A method of preparing a polyose-complex containing product, comprising reacting, in a first step, at least one polyose in an aqueous reaction medium with an activated fatty acid under reactive conditions to obtain a reaction mixture comprising a reaction product of not more than about 10% by weight of fatty acids linked to the polyose through covalent bonds with regard to the total weight of the fatty acids, said reaction mixture further comprising unreacted fatty acid, and, in a second step, subjecting said reaction mixture in the aqueous reaction medium to a lyophilization step.

18. The method of claim 17, wherein said first step is performed by bringing the polyose-containing aqueous reaction medium to an initial basic pH, and then adding said activated fatty acid.

19. The method of claim 17, wherein the reaction mixture contains a polyose-complex and unreacted fatty acid, and prior to lyophilization, the pH of the aqueous reaction medium containing said reaction mixture is neutralized or brought to a basic pH value not greater than about 8.

20. The method of claim 7, wherein said first step is performed at a temperature from ambient to not greater than about 60° C.

21. A method of cosmetic or aesthetic treatment of the skin, comprising applying to the skin a moisture-restoring effective amount of polyose-complex containing product according to claim 1.

22. A polyose complex containing product according to claim 1, wherein said unreacted fatty acid is in the form of a fatty acid salt.

23. A product according to claim 3, wherein the polyose is a heparin.

24. A product according to claim 23, wherein the heparin has a molecular weight between 2,000 and 10,000.

25. A product according to claim 1, wherein the proportion of fatty acid is between 50 and 75% by weight of the total of fatty acid and polyose.

26. A composition according to claim 16, wherein the proportion of fatty acid is between 50 and 75% by weight of the total of fatty acid and polyose.

* * * * *

UNITED STATES PATENT AND TRADEMARK OFFICE
CERTIFICATE OF CORRECTION

PATENT NO. : 5,422,111
DATED : June 06, 1995
INVENTOR(S) : Alain HUC et al.

It is certified that error appears in the above-indentified patent and that said Letters Patent is hereby corrected as shown below:

Title page ,insert item [62] to read:

— — continuation-in-part of PCT/FR92/00054 filed January 22, 1992. — —

Signed and Sealed this

Sixth Day of May, 1997

Attest:

Attesting Officer

BRUCE LEHMAN

Commissioner of Patents and Trademarks